United States Patent [19]

Carling et al.

[11] Patent Number: 5,698,573
[45] Date of Patent: Dec. 16, 1997

[54] IMIDAZOLONE AND OXAZOLONE DERIVATIVES AS DOPAMINE ANTAGONISTS

[75] Inventors: William Robert Carling, Bishops Stortford; Kevin William Moore, Buntingford, both of United Kingdom

[73] Assignee: Merck, Sharp & Dohme, Ltd., Hoddesdon, England

[21] Appl. No.: 615,238

[22] PCT Filed: Sep. 6, 1994

[86] PCT No.: PCT/GB94/01934

§ 371 Date: Mar. 12, 1996

§ 102(e) Date: Mar. 12, 1996

[87] PCT Pub. No.: WO95/07904

PCT Pub. Date: Mar. 23, 1995

[30] Foreign Application Priority Data

Sep. 15, 1993 [GB] United Kingdom ............ 9319126
Apr. 8, 1994 [GB] United Kingdom ............ 9407032

[51] Int. Cl.[6] .............. A61K 31/415; A61K 31/445; C07D 401/04; C07D 413/04
[52] U.S. Cl. .............. 514/326; 514/212; 514/318; 514/320; 514/374; 514/397; 540/603; 546/193; 546/196; 546/210; 548/229; 548/314.7
[58] Field of Search .............. 540/603; 546/196, 546/210, 193; 548/229, 314.7; 514/212, 326, 374, 357, 318, 320

[56] References Cited

U.S. PATENT DOCUMENTS

| | | | |
|---|---|---|---|
| 3,355,457 | 11/1967 | Wright | 548/314.7 |
| 3,455,941 | 7/1969 | Lunsford | 548/229 |
| 4,644,063 | 2/1987 | Masaki | 546/209 |

FOREIGN PATENT DOCUMENTS

95/07905  3/1995  WIPO.

OTHER PUBLICATIONS

Wyngaarden et al. "Cecil Textbook of Medicine" Sauder Co., p. 67, 1983.
Van Kammen "Gamma aminobutyric acid and the dopamine hypothesis of schezophrenia" Ind. Medicus 77:109461, 1977.
Shaywitz et al. "Selective brain dopamine depletion . . . " Ind. Medicus 76:104593, 1976.

*Primary Examiner*—Ceila Chang
*Attorney, Agent, or Firm*—Robert J. North; Melvin Winokur

[57] ABSTRACT

A class of imidazolone and oxazolone derivatives of Structure I,

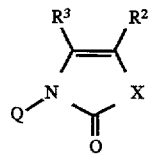

wherein

X represents oxygen or N—$R^1$;

Q represents a substituted five-, six- or seven-membered monocyclic heteroaliphatic ring which contains one nitrogen atom as the sole heteroatom and is linked to the imidazolone or oxazolone ring via a carbon atom;

$R^1$ represents hydrogen or $C_{1-6}$ alkyl; and one of $R^2$ and $R^3$ represents hydrogen or $C_{1-6}$ alkyl and the other of $R^2$ and $R^3$ represents cycloalkyl or a group of formula (i), (ii) or (iii):

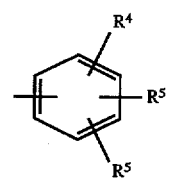

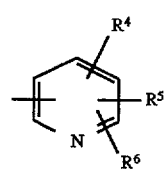

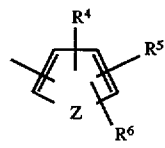

in which Z represents oxygen, sulphur or NH;

$R^4$, $R^5$ and $R^6$ independently represent hydrogen, a hydrocarbon group or a heterocyclic group wherein the hydrocarbon group and heterocyclic group are as defined in the specification; or a pharmaceutically acceptable salt or prodrug thereof, which are ligands for dopamine receptor subtypes within the brain and are therefore of use in the treatment and/or prevention of disorders of the dopamine system, such as schizophrenia.

9 Claims, No Drawings

IMIDAZOLONE AND OXAZOLONE DERIVATIVES AS DOPAMINE ANTAGONISTS

This application is a 371 of PCT/GD94/01934 filed Sep. 6, 1994.

This invention relates to a particular glass of substituted oxazolone and imidazolone derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to $D_2$ receptor blockade in the striatal region of the brain. It is considered (Van Tol et al., supra) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds according to the present invention, being antagonists of dopamine receptor subtypes within the brain, are accordingly of benefit in the treatment and/or prevention of psychotic disorders such as schizophrenia. Moreover, the compounds according to the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

EP-A-0379990 describes a class of 4,5-disubstituted 2H-imidazol-2-ones which are stated to have affinity in vitro against $D_2$, 5-HT$_2$ and $\alpha_1$ receptors, as well as showing activity in vivo on the central nervous system in various behavioural tests, and antihypertensive activity. The compounds described therein are accordingly alleged to be useful as antipsychotic, antidepressant and anxiolytic agents, as well as having utility in the treatment of hypertension and other cardiovascular complaints. Since their antipsychotic activity is presumably mediated by antagonism of $D_2$ receptors, however, it seems reasonable to suppose that these compounds are subject to the drawbacks, in terms of their unpleasant side-effects, customarily associated with classical neuroleptic drugs.

The present invention accordingly provides a compound of formula I, or a salt thereof or a prodrug thereof:

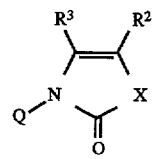

wherein

X represents oxygen or N—R$^1$;

Q represents a substituted five-, six- or seven-membered monocyclic heteroaliphatic ring which contains one nitrogen atom as the sole heteroatom and is linked to the imidazolone or oxazolone ring via a carbon atom;

R$^1$ represents hydrogen or C$_{1-6}$ alkyl; and one of R$^2$ and R$^3$ represents hydrogen or C$_{1-6}$ alkyl and the other of R$^2$ and R$^3$ represents cycloalkyl or a group of formula (i), (ii) or (iii):

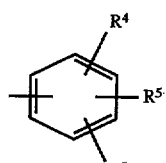

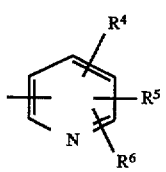

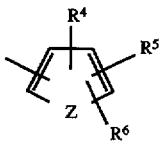

in which Z represents oxygen, sulphur or NH;

R$^4$, R$^5$ and R$^6$ independently represent hydrogen, hydrocarbon, a heterocyclic group, halogen, cyano, trifluoromethyl, nitro, —OR$^a$, —SR$^a$, —SOR$^a$, SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; and R$^a$ and R$^b$ independently represent hydrogen, hydrocarbon or a heterocyclic group.

The monocyclic heteroaliphatic ring Q in the compounds of formula I above represents a substituted pyrrolidyl, piperidyl or homopiperidyl moiety linked through carbon. Examples of suitable rings include the moieties of formula Qa to Qf:

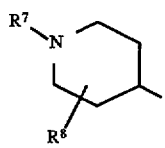

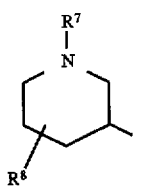
(Qb)

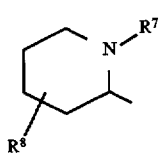
(Qc)

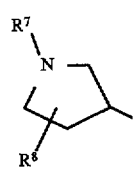
(Qd)

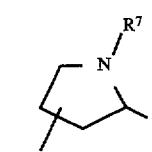
(Qe)

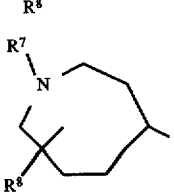
(Qf)

wherein one of $R^7$ and $R^8$ represents hydrocarbon or a heterocyclic group, and the other of $R^7$ and $R^8$ represents hydrogen, hydrocarbon or a heterocyclic group.

A particular monocyclic heteroaliphatic ring represented by the substituent Q in formula I is the ring of structure Qa above.

The compounds of the present invention are preferably prepared and utilised in the form of a free base or as a pharmaceutically acceptable salt thereof.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R'", —NR'COR'", —NR'CO$_2$R'", —NR'SO$_2$R'", —CH$_2$NR'SO$_2$R'", —NHCONR'R'", —CONR'R'", —SO$_2$NR'R'" and —CH$_2$SO$_2$NR'R'", in which R' and R'" independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Preferably, X represents N—$R^1$ in which the substituent $R^1$ suitably represents hydrogen or methyl, especially hydrogen.

Suitably, one of $R^2$ and $R^3$ represents hydrogen or methyl, and the other of $R^2$ and $R^3$ represents a group of formula (i) as defined above.

Suitably, Z is oxygen or sulphur.

Suitable values for the substituents $R^4$, $R^5$ and $R^6$ include hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, methoxy, benzyloxy, fluoro and chloro.

Suitable values for the substituents $R^7$ and $R^8$ include $C_{2-6}$ alkenyl, $C_{3-7}$ cycloalkyl($C_{1-6}$)alkyl, aryl and aryl($C_{1-6}$)alkyl, any of which groups may be optionally substituted. In addition, one of $R^7$ and/or $R^8$ may represent hydrogen. Examples of suitable substituents on the groups $R^7$ and/or $R^8$ include $C_{1-6}$ alkyl, halogen, trifluoromethyl, $C_{1-6}$ alkoxy, $C_{1-3}$ alkylenedioxy, cyano and nitro.

Particular values of $R^7$ and $R^8$ include hydrogen, allyl, cyclopropylmethyl, cyclohexylmethyl, benzyl, methylbenzyl, chlorobenzyl, bromobenzyl, iodobenzyl, dichlorobenzyl, methoxy-benzyl, trifluoromethyl-benzyl, methylenedioxy-benzyl, cyanobenzyl, nitro-benzyl, naphthylmethyl, phenethyl and phenylpropyl, provided that at least one of $R^7$ and $R^8$ is other than hydrogen. Suitably, one of $R^7$ and $R^8$ represents hydrogen, and the other of $R^7$ and $R^8$ is other than hydrogen. Preferably, $R^8$ represents hydrogen and $R^7$ is other than hydrogen.

A particular sub-class of compounds according to the invention is represented by the compounds of formula IIA, and salts and prodrugs thereof:

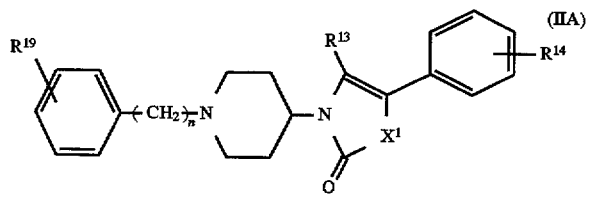

(IIA)

wherein n is zero, 1, 2 or 3;

$X^1$ represents oxygen or N—$R^{11}$;

$R^{11}$ and $R^{13}$ independently represent hydrogen or $C_{1-6}$ alkyl; and $R^{14}$ and $R^{19}$ independently represent hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

Preferably, $X^1$ is N—$R^{11}$ in which $R^{11}$ suitably represents hydrogen or methyl, especially hydrogen.

Suitably, $R^{13}$ represents hydrogen or methyl.

Particular values of $R^{14}$ include hydrogen, fluoro, chloro, methyl, ethyl, methoxy and benzyloxy.

Particular values of $R^{19}$ include hydrogen, methyl, ethyl, chloro, bromo, iodo, trifluoromethyl, methoxy, ethoxy, cyano, nitro and dimethylamino.

Another sub-class of compounds according to the invention is represented by the compounds of formula IIB, and salts and prodrugs thereof:

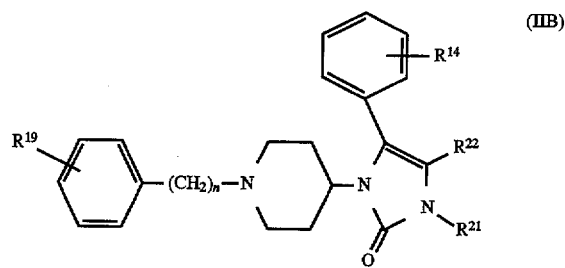

(IIB)

wherein n, $R^{14}$ and $R^{19}$ are as defined with reference to formula IIA above; and $R^{21}$ and $R^{22}$ independently represent hydrogen or $C_{1-6}$ alkyl.

Suitably, $R^{21}$ and $R^{22}$ independently represent hydrogen or methyl.

Specific compounds within the scope of the present invention include:

1-(1-benzylpiperidin-4-yl)-5-methyl-4-phenyl-1,3-dihydroimidazol-2-one;

1-(1-benzylpiperidin-4-yl)-4-methyl-5-phenyl-1,3-dihydroimidazol-2-one;

1-(1-benzylpiperidin-4-yl)-4-(4-chlorophenyl)-5-methyl-1,3-dihydroimidazol-2-one;

1-(1-benzylpiperidin-4-yl)-5-(4-chlorophenyl)-4-methyl-1,3-dihydroimidazol-2-one;

1-(1-benzylpiperidin-4-yl)-4-phenyl-1,3-dihydroimidazol-2-one;

1-(1-benzylpiperidin-4-yl)-3-methyl-4-phenyl-1,3-dihydroimidazol-2-one;

1-(1-benzylpiperidin-4-yl)-3,5-dimethyl-4-phenyl-1,3-dihydroimidazol-2-one;

5-methyl-4-phenyl-1-[1-(2-phenylethyl)piperidin-4-yl]-1,3-dihydroimidazol-2-one;

5-methyl-1-[1-(2-methylbenzyl)piperidin-4-yl]-4-phenyl-1,3-dihydroimidazol-2-one;

4-(4-chlorophenyl)-5-methyl-1-[1-(2-phenylethyl)-piperidin-4-yl]-1,3-dihydroimidazol-2-one;

4-methyl-5-phenyl-3-[1-(2-phenylethyl)piperidin-4-yl]-3H-oxazol-2-one;

4-(4-chlorophenyl)-5-methyl-1-[1-(2-methylbenzyl)-piperidin-4-yl]-1,3-dihydroimidazol-2-one;

5-methyl-1-[1-(2-methylbenzyl)piperidin-4-yl]-4-(4-methylphenyl)-1,3-dihydroimidazol-2-one;

1-[1-(3-cyanobenzyl)piperidin-4-yl]-5-methyl-4-phenyl-1,3-dihydroimidazol-2-one;

1-[1-(3-methoxybenzyl)piperidin-4-yl]-5-methyl-4-phenyl-1,3-dihydroimidazol-2-one;

1-[1-(3-chlorobenzyl)piperidin-4-yl]-5-methyl-4-phenyl-1,3-dihydroimidazol-2-one;

1-[1-(3-bromobenzyl)piperidin-4-yl]-5-methyl-4-phenyl-1,3-dihydroimidazol-2-one;

1-[1-(3-iodobenzyl)piperidin-4-yl]-5-methyl-4-phenyl-1,3-dihydroimidazol-2-one;

5-methyl-4-phenyl-1-[1-(3-trifluoromethylbenzyl)-piperidin-4-yl]-1,3-dihydroimidazol-2-one;

5-methyl-1-[1-(2,3-methylenedioxybenzyl)piperidin-4-yl]-4-phenyl-1,3-dihydroimidazol-2-one;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention in which X is NH may be prepared by a process which comprises reacting a compound of formula III with a compound of formula IV:

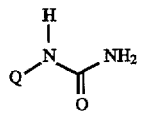
(III)

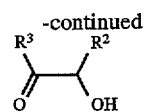
(IV)

wherein Q, $R^2$ and $R^3$ are as defined above; followed, if necessary, by separation of the resulting mixture of isomers by conventional means.

The reaction is conveniently carried out under standard conditions capable of promoting the condensation reaction. Suitable reaction conditions comprise heating the reagents in toluene at reflux in the presence of trifluoroacetic acid, with azeotropic removal of water, advantageously in a Dean-Stark apparatus.

As indicated above, the overall reaction between compounds III and IV will usually give rise to a mixture of isomeric products of formula I, in one of which $R^2$ represents hydrogen or $C_{1-6}$ alkyl and $R^3$ represents cycloalkyl or a group of formula (i), (ii) or (iii) as defined above, and in the other of which these substituents are reversed. For this reason, it will generally be necessary to separate the mixture of isomers obtained therefrom by conventional methods such as column chromatography.

The compounds of formula III above may be prepared by reacting a compound of formula Q—$NH_2$ with a compound of formula $R^P$—N=C=O, wherein Q is as defined above, and $R^P$ represents an amino-protecting group; followed by removal of the amino-protecting group $R^P$.

The reaction is conveniently carried out by stirring the reactants in an inert solvent such as dichloromethane, typically at 0° C. with warming to room temperature.

The amino-protecting group $R^P$ is suitably an acyl moiety such as benzoyl, which can conveniently be removed as necessary by treatment under basic conditions, e.g. sodium methoxide in methanol, or sodium hydroxide in aqueous methanol.

In an alternative procedure, the compounds according to the invention wherein X represents N—$R^1$ may be prepared by a process which comprises reacting a compound of formula $R^{10}$—N=C=O with a compound of formula V:

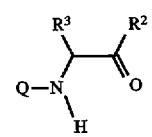
(V)

wherein Q, $R^2$ and $R^3$ are as defined above, and $R^{10}$ corresponds to the group $R^1$ or represents an amino-protecting protecting group $R^P$ as defined above; followed, where necessary, by removal of the amino-protecting group $R^{10}$; and subsequently, if desired, N-alkylation by standard methods to introduce the moiety $R^1$.

The reaction is conveniently effected by a multi-step procedure which comprises stirring the reactants in a lower alkanol such as methanol; concentrating the reaction mixture in vacuo before treating with a base such as sodium methoxide in methanol; and then treating with trifluoroacetic acid to effect dehydration with concomitant ring closure.

The intermediates of formula V may conveniently be prepared by reacting a compound of formula Q—$NH_2$ with a compound of formula VI:

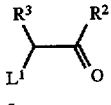
(VI)

wherein Q, $R^2$ and $R^3$ are as defined above, and $L^1$ represents a suitable leaving group.

The leaving group $L^1$ is suitably a halogen atom, e.g. bromine, in which case the reaction is conveniently effected by stirring the reagents under basic conditions in an inert solvent, for example triethylamine in dichloromethane.

In a further procedure, the compounds according to the invention wherein X is oxygen may be prepared by a process which comprises reacting a compound of formula V as defined above with a compound of formula $L^2$—CO—$L^3$, wherein $L^2$ and $L^3$ independently represent suitable leaving groups.

The leaving groups $L^2$ and $L^3$ are suitably selected from halogen atoms, e.g. chlorine or bromine, and $C_{1-4}$ alkoxy groups such as methoxy or ethoxy. A typical reagent of formula $L^2$—CO—$L^3$ is methyl chloroformate.

The reaction is conveniently carried out by stirring the reactants, typically with the reagent of formula $L^2$—CO—$L^3$ in excess, in an inert solvent such as dichloromethane; and then treating the reaction mixture with a base such as sodium methoxide in methanol, in order to effect the required ring closure.

If desired, the intermediates of formula V above, where they are stable, may be isolated as such before reaction with the appropriate compound of formula $R^{10}$—N=C=O or $L^2$—CO—$L^3$. More typically, however, the final product may be obtained directly from the intermediates of formula VI above in a "one-pot" procedure without isolation of the intermediates of formula V.

Where they are not commercially available, the starting materials of formula IV, VI, Q—$NH_2$, $R^{10}$—N=C=O and $L^2$—CO—$L^3$ may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

In particular, a compound of formula I wherein Q represents a five-, six- or seven-membered aza-aliphatic ring substituted on the sole ring nitrogen atom by a benzyl group initially obtained may be converted into a further compound of formula I wherein Q is substituted on the ring nitrogen atom by a group other than benzyl by a stepwise procedure which comprises removal of the benzyl group followed by attachment of the ring nitrogen substituent by conventional methods. Removal of the benzyl group is conveniently effected by treatment with 1-chloroethyl chloroformate, followed by heating in methanol. Attachment of a substituent to the debenzylated ring nitrogen atom can then be effected, in the case of an alkyl or substituted-alkyl substituent, by reaction with an alkyl halide, typically under basic conditions, e.g. in the presence of ethyldiisopropylamine (Hünig's base), in a suitable solvent such as N,N-dimethylformamide; or under reductive amination conditions, whereby the appropriate aldehyde is reacted with the debenzylated amine in the presence of a reducing agent such as sodium cyanoborohydride.

Similarly, a compound of formula I wherein $R^1$ is hydrogen initially obtained may be converted into a compound of formula I wherein $R^1$ represents $C_{1-6}$ alkyl by standard alkylation techniques, such as by treatment with an alkyl iodide, e.g. methyl iodide, typically under basic conditions, e.g. sodium hydride in N,N-dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

1-(1-Benzyl-piperidin-4-yl)-5-methyl-4-phenyl-1,3-dihydroimidazol-2-one

Method A a) 4-(Phenylcarbonylaminocarbonyl)amino-1-benzyl-piperidine

To an ice-bath cooled solution of benzoyl isocyanate (7.725 ml, 0.0525 Mol) in dichloromethane (400 ml) was added 4-amino-1-benzyl piperidine (10 g, 10.72 ml, 0.0525 Mol) dropwise. When the addition was complete the solution was allowed to stir at room temperature for 1 h then the solvent was removed by rotary evaporation. The residue was triturated with diethyl ether and collected by filtration to give the required product as a white solid 15.4 g (87%). Mp. 179°–180° C. $^1$H NMR (DMSO) δ 1.51 (2H, m), 1.86 (2H, m), 2.14 (2H, m), 2.69 (2H, m), 3.47 (2H, s), 3.65 (1H, m), 7.24–7.33 (5H, m), 7.50 (2H, t, J=7.9 Hz), 7.61 (1H, t, J=7.9 Hz), 7.96 (2H, d, J=7.9 Hz), 8.69 (1H, d, J=7.8 Hz), 10.67 (1H, br s); MS (CI) m/e 338 [MH]$^+$. Anal. Found C, 70.99; H, 6.86; N, 12.41. $C_{20}H_{23}N_3O_2$ requires C, 71.19; H, 6.87; N, 12.45%.

b) 4-(Aminocarbonyl)amino-1-benzyl-piperidine

The product from Example 1, Method A, Step a (15g, 0.0445 Mol) was dissolved in 50% aqueous methanol (400 ml) with sodium hydroxide (30 g) and stirred at room temperature for 48 h. The solvents were removed in vacuo, the residue obtained was suspended in water and heated at reflux for 1 h. After allowing to cool, the required product was collected by filtration and washed with diethyl ether (10.4 g, 99%). Mp 148° C. $^1$H NMR (DMSO) δ 1.30 (2H, m), 1.71 (2H, m), 1.99 (2H, m), 2.68 (2H, m), 3.32 (1H, m), 3.42 (2H, s), 5.32 (2H, br s), 5.86 (1H, d, 7.8 Hz), 7.21–7.34 (5H, m); MS (CI) m/e 234 [MH]$^+$. Anal. Found C, 67.25; H, 8.43; N, 18.00. $C_{20}H_{23}N_3O_2$ requires C, 66.92; H, 8.20 N, 18.01% c) 1-(1-Benzyl-piperidin-4-yl)-5-methyl-4-phenyl-1,3-dihydroimidazol-2-one

The product from Example 1, Method A, Step b (1.86 g, 0.008 Mol) and 2-hydroxypropiophenone (1.86 g, 0.008 Mol) were suspended in toluene (15 ml) with trifluoroacetic acid (3 ml) and heated under reflux, using a Dean-Stark trap, for 2 h. The solvents were removed under vacuum and the residue was partitioned between dichloromethane (2×40 ml) and 1N sodium hydroxide solution (1×30 ml). The combined organic layers were washed with brine (1×30 ml), dried (MgSO$_4$), filtered and concentrated under vacuum. The residue was purified by flash silica chromatography using 0–5% methanol in dichloromethane as eluent to give the title compound as the less polar isomer. This was recrystallised from ethyl acetate to give the required compound as a white solid (0.045 g, 2%). Mp 230° C. dec. $^1$H NMR (DMSO) δ 1.60 (2H, m), 2.02 (2H, m), 2.20 (3H, s), 2.43 (2H, m), 2.89 (2H, m), 3.49 (2H, s), 3.75 (1H, m), 7.21–7.40 (10H, m), 10.25 (1H,br s). The regiochemistry of this compound was assigned by observation of an NOE between the methyl protons at δ 2.20 and the piperidine methine proton at δ 3.75; MS (CI) m/e 348 [MH]$^+$. Anal. Found C, 75.38; H, 7.30; N, 11.83. $C_{22}H_{25}N_3O$. 0.1 H$_2$O requires C, 75.66; H, 7.27; N, 12.03%.

Method B

To a solution of 4-amino-1-benzyl piperidine (4 g, 4.28 ml, 0.021 Mol) in dichloromethane (40 ml) was added 2-bromopropiophenone (4.48 g, 0.021 Mol) and triethylamine (2.8 ml, 0.046 Mol) and the reaction mixture was stirred for 14 h. Benzoylisocyanate (3.41 g, 0.021 Mol) was added and the solution was stirred for a further 1 h. Methanol (20 ml) was added and the solvents were removed in vacuo. The residue was redissolved in methanol (60 ml) and sodium methoxide (5.8 g, 0.93 mol) was added. After stirring for 1 h, trifluoroacetic acid (20 ml) was added and after a further 0.5 h, the reaction mixture was concentrated under vacuum. The residue was partitioned between dichloromethane (150 ml)and saturated potassium carbonate solution (80 ml) then dried (MgSO$_4$), filtered and concentrated in vacuo. Silica gel chromatography using 0–5% methanol/dichloromethane as eluent followed by recrystallisation from methanol/ethyl acetate gave the required compound (1.2 g, 16%) which was identical with the product obtained using Method A.

Repeating this reaction under the same conditions using 44 g of 2-bromopropiophenone (0.2 mol) and 35 ml of 4-amino-1-benzylpiperidine (0.17 mol) in dichloromethane (500 ml) with 60 ml of triethylamine (0.43 mol) followed by 25.3 g of benzolyisocyanate (0.17 mol) and 28 g of sodium methoxide (27 g, 0.5 mol) in methanol (500 ml) produced the required compound (45 g, 76%). 37 g of the compound recrystallised out after work up and was collected by filtration. The remaining 8 g was isolated using chromatography.

EXAMPLE 2

1-(1-Benzyl-piperidin-4-yl)-4-methyl-5-phenyl-1,3-dihydroimidazol-2-one

The more polar compound from Example 1, Method A, Step c, was recrystallised from methanol/ethyl acetate to give the title compound as a white solid (0.24 g, 9%). Mp 249° C. $^1$H NMR (DMSO) δ 1.49 (2H, m), 1.74 (2H, m), 1.89 (3H, s), 2.45 (2H, m), 2.79 (2H, m), 3.49 (1H, m), 3.38 (2H, s), 7.20–7.47 (10H, m), 10.05 (1H,br s); MS (CI) m/e 348 [MH]$^+$. Anal. Found C, 76.05; H, 7.25; N, 12.08. $C_{22}H_{25}N_3O$. requires C, 76.05; H, 7.25; N, 11.83%.

EXAMPLE 3

1-(1-Benzyl-piperidin-4-yl)-5-methyl-4-(4-chlorophenyl)-1,3-dihydro-imidazol-2-one This compound was prepared and isolated as the less polar regioisomer using the procedure described in Example 1, Method A, Step c, using 4'-chloro-2-hydroxypropiophenone instead of 2-hydroxypropiophenone. Mp 240° C. dec. $^1$H NMR (DMSO) δ 1.60 (2H, m), 2.02 (2H, m), 2.19 (3H, s), 2.42 (2H, m), 2.89 (2H, m), 3.49 (2H, s), 3.75 (1H, m), 7.25–7.44 (10H, m), 10.31 (1H, br s); MS (CI) m/e 384 & 382 [MH]$^+$. Anal. Found C, 69.00; H, 6.21; N, 10.80. $C_{22}H_{24}ClN_3O$ requires C, 69.19; H, 6.33; N, 11.00%.

EXAMPLE 4

1-(1-Benzyl-piperidin-4-yl )-4-methyl-5-(4-chlorophenyl )-1,3-dihydro-imidazol-2-one This compound was prepared and isolated as the more polar regioisomer using the procedure described in Example 1, Method A, Step c, using 4'-chloro-2-hydroxypropiophenone instead of 2-hydroxypropiophenone. Mp 270°–271° C. dec. $^1$H NMR (DMSO) δ 1.49 (2H, m), 1.77 (2H, m), 1.84 (3H, s), 2.43 (2H, m), 2.79 (2H, m), 3.31 (1H, m), 3.39 (2H, s), 7.20–7.32 (8H, m), 7.51 (2H, d, J= 7.8 Hz), 10.11 (1H, br s). The regiochemistry of this compound was assigned by observation of an NOE between the methyl protons at δ1.84 and the NH proton at δ 10.11; MS (CI) m/e 384 & 382 [MH]$^+$. Anal. Found C, 68.58; H, 6.23; N, 10.73. $C_{22}H_{24}ClN_3O$. 0.25H$_2$O requires C, 68.38; H, 6.39; N, 10.87%.

EXAMPLE 5

1-(1-Benzyl-piperidin-4-yl)-4-phenyl-1,3-dihydro-imidazol-2-one

Method A

This compound was prepared using the procedure described in Example 1, Method B, using 2-bromoacetophenone instead of 2-bromopropiophenone. Mp 306°–308° C. $^1$H NMR (DMSO+NaOD) δ 1.65 (4H, m), 2.03 (2H, m), 2.88 (2H, m), 3.48 (2H, s), 3.82 (1H, m), 6.73 (1H, s), 6.94–7.62 (10H, m), MS (CI) m/e 334 [MH]$^+$. Anal. Found C, 68.00; H, 6.70; N, 11.13. $C_{21}H_{23}N_3O$ requires C, 68.19; H, 6.54; N, 11.36%.

Method B

This compound was also prepared using the procedure described in Example 1, Method B, using trimethylsilylisocyante instead of benzoylisocyanate to give a product which was identical to the product obtained using Method A.

EXAMPLE 6

1-(1-Benzyl-piperidin-4-yl)-3-methyl-4-phenyl-1,3-dihydroimidazol-2-one hydrochloride This compound was prepared using the procedure described in Example 1, Method B, using 2-bromoacetophenone instead of 2-bromopropiophenone and methyl isocyanate instead of benzoyl isocyanate and was purified as a hydrochloride salt. Mp 227° C. dec. $^1$H NMR (DMSO) δ 2.00 (2H, m), 2.29 (2H, m), 3.15 (2H, m), 3.33 (3H, s), 3.38 (2H, m), 4.20 (1H, m), 4.30 (2H, s), 6.61 (1H, s), 7.35–7.70 (10H, m), 10.96 (1H,br s); MS (CI) m/e 348 [MH]$^+$. Anal. Found C, 67.80; H, 7.13; N, 10.49. $C_{22}H_{25}N_3O$. HCl. 0.4H$_2$O requires C, 67.56; H, 6.91; N, 10.74%.

EXAMPLE 7

1-(1-Benzyl-piperidin-4-yl)-3,5-dimethyl-4-phenyl-1,3-dihydro-imidazol-2-one hydrochloride This compound was prepared using the procedure described in Example 1, Method B, using methyl isocyanate instead of benzoyl isocyanate and was purified as a hydrochloride salt. Mp 295° C. dec. $^1$H NMR (DMSO+NaOD) δ 1.62 (2H, m), 2.04 (2H, m), 2.06 (3H, s), 2.40 (2H, m), 2.90 (2H, m), 3.33 (3H, s), 3.49 (2H, s), 3.79 (1H, m), 7.24–7.49 (10H, m), 10.96 (1H,br s); MS (CI) m/e 362 [MH]$^+$. Anal. Found C, 69.56; H, 7.41; N, 10.45. $C_{23}H_{27}N_3O$. HCl requires C, 69.41; H, 7.09; N, 10.56%.

EXAMPLE 8

5-Methyl-1-(1-phenethyl-piperidin-4yl)-4-phenyl-1,3-dihydro-imidazol-2-one a) 1-Benzyl-4-$^t$butyloxycarbonylamino-piperidine.

To a solution of 1-benzyl-4-amino-piperidine (40 g, 0.21 Mol) in dichloromethane (500 ml) was added di-tert-butyldicarbonate (50.4 g, 0.23 Mol) and the reaction mixture was stirred under nitrogen for 18 h at room temperature. The solvent was removed by rotary evaporation and the residue was triturated with diethyl ether then collected by filtration to give the required product as a white solid 60.29 g (99%) Mp. 135°–138° C. $^1$H NMR (CDCl$_3$) δ 1.44 (9H,m), 1.53 (2H,m), 1.92 (2H,s), 2.12 (2H,m), 2.83 (2H,m) 3.51 (2H,s) 4.42 (1H,s) 7.22–7.32 (5H,m).

b) 4-$^t$Butyloxycarbonylamino-piperidine

To a suspension of 1-benzyl-4-$^t$butyloxycarbonylamino-piperidine (60.29 g, 0.20 Mol) in methanol (700 ml) was added (under nitrogen) 10% palladium on carbon catalyst (3.0 g) and the mixture was shaken under 50 psi of hydrogen for 18 h. The solution was filtered and the solvent was removed by rotary evaporation to give the title compound as a white solid (40 g, 97%). Mp. 153°–155° C. $^1$H NMR (CDCl$_3$) δ 1.43 (9H,s), 1.97(4H,s), 2.65(2H,m), 3.60 (2H, m), 4.47 (1H,s).

c) 4-Amino-1-phenylethyl-pineridine hydrochloride

To a suspension of 4-$^t$butyloxycarbonylamino-piperidine (3.5 g, 0.0175 Mol) in dimethylformamide (10 ml) was added ethyldiisopropylamine (6.1 ml, 0.035 Mol) and 2-bromoethylbenzene (2.64 ml, 0.0193 Mol) and the solution was stirred at room temperature for 42 h under nitrogen. The reaction mixture was poured into water (500 ml) and extracted with dichloromethane (3×250 ml). The combined organic layers were washed with brine (1×30 ml) then dried (MgSO$_4$), filtered and concentrated under vacuum. The residue was triturated with diethyl ether hexane (1:1) and collected by filtration to give the required product as a white solid, which was dissolved in a saturated solution of hydrogen chloride in methanol (100 ml) and stirred at room temperature for 18 h. The solvent was removed by rotary evaporation then the residue was triturated with diethyl ether and collected by filtration to give the required product as a white solid (1.55 g, 39%). Mp. 200°–201° C. $^1$H NMR δ 1.89 (2H,m), 2.80 (2H,m), 3.04 (2H,m), 3.30 (2H,m), 3.64 (1H,m), 3.72(2H,s) 3.86 (2H,s), 7.26–7.44 (5H,m).

d) 5-Methyl-1-(1-phenethyl-piperidin-4-yl)-4-phenyl-1,3-dihydro-imidazol-2-one

This compound was prepared using the procedure described in Example 1, Method B, using 4-amino-1-phenylethyl-piperidine hydrochloride and an extra equivalent of triethylamine, instead of 4-amino-1-benzyl piperidine. Mp 232°–236° C. $^1$H NMR (DMSO) δ 1.60 (2H, m), 2.04 (2H, m), 2.21 (3H, s), 2.40 (6H, m), 2.74 (2H, m), 3.05 (2H,m), 3.75 (1H, m), 7.16–7.40 (10H, m), 10.23 (1H,br s); MS (CI) m/e 362 [MH]$^+$. Anal. Found C, 76.13; H, 7.36; N, 11.43. $C_{23}H_{27}N_3O$ requires C, 76.42; H, 7.53; N, 11.62%.

EXAMPLE 9

5-Methyl-1-(1-(2-methylbenzyl)-piperidin-4-yl)-4-phenyl-1,3-dihydro-imidazol-2-one a) 4-Amino-1-(2-methylbenzyl)-piperidine hydrochloride This compound was prepared using the procedure described in Example 8, part c, using α-bromo-o-xylene instead of bromoethylbenzene. Mp. 276°–278° C. $^1$H NMR δ 2.08 (4H,m), 2.42 (3H,s), 3.16 (4H,m), 3.38 (2H,s), 4.26(1H,m), 7.26–7.49 (4H,m), 8.35 (2H,s).

b) 5-Methyl-1-(1-(2-methylbenzyl)-piperidin-4-yl)-4-phenyl-1,3-dihydro-imidazol-2-one This compound was prepared using the procedure described in Example 1, Method B, using 4-amino-1-(2-methylbenzyl)piperidine hydrochloride and an extra equivalent of triethylamine, instead of 4-amino-1-benzyl piperidine. Mp 218°–220° C. $^1$H NMR (DMSO) δ 1.58 (2H, m), 2.02 (2H, m), 2.08 (3H s), 2.19 (3H, s), 2.37 (2H, m), 2.87 (2H, m), 3.43 (2H, s), 3.76 (1H, m), 7.12–7.42 (9H, m), 10.25 (1H,br s); MS (CI) m/e 362 [MH]$^+$. Anal. Found C, 76.15; H, 7.27; N, 11.33. $C_{23}H_{27}N_3O$. requires C, 76.42; H, 7.53; N, 11.62%.

EXAMPLE 10

1-(4-Chlorophenyl)-1-(1-phenethyl-piperidin-4-yl)-5-methyl-1,3-dihydro-imidazol-2-one This compound was prepared using the procedure described in Example 1, Method B, using 4-amino-1-phenylethyl-piperidine hydrochloride instead of 4-amino-1-benzyl piperidine and 2-bromo-1-(4-chlorophenyl)-1-carbonyl-propane and an extra equivalent of triethylamine, instead of 2-bromopropiophenone. Mp. 229°–231° C. $^1$H NMR δ 1.62 (2H,m), 2.03(2H, m), 2.19(3H, s), 2.27(2H, m), 2.60 (2H,m), 3.05(2H, s), 3.30(2H, s), 3.74(1H, m), 7.18–7.45(9H, m); MS (CI) m/e 396 [MH]$^+$. Anal Found C, 68.13; H, 6.74; N, 10.22. $C_{23}H_{26}N_3OCl.0.45H_2O$ requires C, 68.37; H, 6.71; N, 10.40%.

EXAMPLE 11

4-Methyl-3-(1-phenethyl-piperidin-4-yl)-5-phenyl-3H-oxazol-2-one

To a solution of a 4-amino-1-phenethyl-piperidine hydrochloride (Example 8c, 2 g, 0.0072 Mol) and triethylamine (3.31 ml, 3.3 Mol eq) in dichloromethane (30 ml) was added 2-bromopropiophenone (1.54 g, 1 Mol eq) and the reaction mixture was stirred for 14 h at room temperature. After ice-bath cooling, methylchloroformate (3.36 ml, 6 Mol eq) was added and the reaction mixture stirred for a further 1 h. Triethylamine (5 ml) was added and the reaction mixture was concentrated in vacuo. The residue was redissolved in methanol (50 ml) and sodium methoxide (3 g) was added. After stirring at room temperature for 0.5 h, the reaction mixture was heated under reflux for 1h. After cooling, the solution was concentrated under vacuum and the residue obtained was partitioned between dichloromethane and water then dried (MgSO$_4$), filtered and evaporated. The crude product was purified on a silica gel column using 0 to 2% methanol in dichloromethane as eluent then recrystallised from diethyl ether/hexane to give the title compound as a colourless solid (0.14 g, 5%). Mp 144° C. $^1$H NMR (DMSO) δ 1.72 (2H, m), 2.08 (2H, m), 2.30 (3H s), 2.33 (2H, m), 2.50 (2H, m), 2.75 (2H, m), 3.04 (2H, s), 3.69 (1H, m), 7.16–7.33 (5H, m), 7.42–7.47 (5H, m); MS (CI) m/e 363 [MH]$^+$. Anal. Found C, 76.10; H, 7.19; N, 7.61. $C_{23}H_{26}ClN_3O$. 0.35H$_2$O requires C, 76.21; H, 7.23; N, 7.73%.

EXAMPLE 12

4-(4-Chlorophenyl)-5-methyl-1-[1-(2-methylbenzyl)-piperidin-4-yl]-1,3-dihydro-imidazol-2-one This compound was prepared using the procedure described in Example 1, Method B, using 4-amino-1-(2-methylbenzyl)-piperidine (obtained by partition of 9a between dichloromethane and 1N sodium hydroxide solution) instead of 4-amino-1-benzyl piperidine and 2-bromo-4'-chloro-propiophenone instead of 2-bromopropiophenone. Mp 218°–220° C. $^1$H NMR (DMSO)) δ 1.60 (2H, m), 2.06 (2H, m), 2.19 (3H s), 2.32 (3H, s), 2.39 (2H, m), 2.89 (2H, m), 3.44 (2H, s), 3.77 (1H, m), 7.15 (4H, m), 7.24 (1H, m), 7.38 (2H, d, J=7.8 Hz), 7.41 (2H, d, J=7.8 Hz), 10.32 (1H,br s); MS (CI) m/e 398 and 396 [MH]$^+$. Anal. Found C, 78.28; H, 6.27; N, 10.29. $C_{23}H_{26}ClN_3O$. 0.35H$_2$O requires C, 68.68; H, 6.69; N, 10.45%.

EXAMPLE 13

5-Methyl-1-[1-(2-methylbenzyl)-piperidin-4-yl]-4-(4-methylphenyl)-1,3-dihydro-imidazol-2-one This compound was prepared using the procedure described in Example 1, Method B, using 4-amino-1-(2-methylbenzyl)-piperidine (obtained by partition of 9a between dichloromethane and 1N sodium hydroxide solution)instead of 4-amino-1-benzylpiperidine and 2-bromo-4'-methyl-propiophenone instead of 2-bromopropiophenone. Mp 262° C. $^1$H NMR (DMSO) δ 1.60 (2H, m), 2.05 (2H, m), 2.17 (3H, s), 2.29 (3H, s), 2.34 (3H, s), 2.37 (2H, m), 2.88 (2H, m), 3.43 (2H, s), 3.75 (1H, m), 7.14–7.24 (8H, m), 10.20 (1H, s); MS (CI) m/e 376 [MH]$^+$. Anal. Found C, 77.00; H, 7.88; N, 11.11. $C_{24}H_{29}N_3O$ requires C, 76.76; H, 7.78; N, 11.19%.

EXAMPLE 14 a) 5-Methyl-4-phenyl-1-(1H)-piperidin-4-yl-1,3-dihydroimidazol-2-one Hydrochloride The product from Example 1, Method B (40 g, 0.115 mol) was dissolved in dichloromethane (600 ml) at 0° C. and 1-chloroethylchloroformate (18.66 ml, 1.5 molar equivalents) was added dropwise over 15 mins. The reaction mixture was allowed to warm to room temperature and stirred for 14 h. The solvents were removed under vacuum and the residue was redissolved in methanol (500 ml) and heated under reflux for 2 h. After cooling, the solid produced was collected by filtration and recrystallised from methanol to give the title compound as a white solid (23.14 g, 68%). $^1$H NMR (DMSO) δ 1.83 (2H, m), 2.22 (3H, s), 2.66 (2H, m), 3.00 (2H, m), 3.34 (2H, m), 4.10 (1H, m), 7.22–7.44 (5H, m), 8.66 (1H, br s), 9.31 (1H, br s), 10.36 (1H, s); MS (CI) m/e 258 (MH)$^+$.

b) 5-Methyl-4-phenyl-1-(1H)-piperidin-4-yl-1,3-dihydroimidazol-2-one

The product from Example 14, part a (23.1 g) was added to aqueous sodium hydroxide (800 ml of 1 molar solution) and the aqueous solution was extracted with dichloromethane (4×200 ml), the combined organic layers were washed with brine (1×200 ml), dried (MgSO$_4$), filtered and concentrated under vacuum to yield the required product (16 g, 80%), m.p. 235–238° C.

c) 1-(3-Cyanobenzylpiperidin-4-yl)-5-methyl-4-phenyl-1,3-dihydro-imidazol-2-one To a solution of the product from Example 14, part b (1.0 g, 3.9 mmol) in anhydrous dimethylformamide (50 ml) was added α-bromo-m-tolunitrile (0.84 g, 4.4 mmol) and ethyl-diisopropylamine (1.35 ml, 7.8 mmol) and the reaction mixture was stirred at room temperature for 18 hrs under nitrogen. This mixture was poured into sodium hydroxide solution (200 ml, 1M) and extracted into dichloromethane (3×100 ml). The combined organic layers were washed with brine (2×100 ml), dried (MgSO$_4$) and the solvent was removed by rotary evaporation to yield the crude product which was recrystallised from ethyl acetate/hexane to yield the required product (0.86 g, 60%), m.p. 254°–256° C. (dec.). $^1$H NMR (DMSO) δ 1.61 (2H, d, J=11 Hz), 2.06 (2H, m), 2.19 (3H, s), 2.44 (2H, m), 2.88 (2H, d, J=11 Hz), 3.56 (2H, s), 3.75 (1H, m), 7.21–7.75 (9H, m), 10.26 (1H, s); MS (CI) m/e 373 [MH]$^+$. Anal. Found C, 73.97; H, 6.23; N, 14.90. $C_{23}H_{24}N_4O$ requires C, 74.17; H, 6.50; N, 15.04%.

EXAMPLE 15

1-(3-Methoxy-benzylpiperidin-4-yl)-5-methyl-4-phenyl-1,3-dihydro-imidazol-2-one This compound was prepared using the procedure described in Example 14, part C using 3-methoxybenzylbromide instead of α-bromo-m-tolunitrile. m.p. 227–228° C. $^1$H NMR (DMSO) δ 1.6 (2H, d, J=10 Hz), 2.01 (2H, m), 2.19 (3H, s), 2.4 (2H, m), 2.9 (2H, d, J=11 Hz), 3.46 (2H, s), 3.75 (4H, m), 6.8–6.9 (3H, m), 7.21–7.4 (6H, m), 10.26 (1H, s). MS (CI) m/e 378 [MH]$^+$. Anal. found C, 73.32; H, 7.26; N, 11.00. $C_{23}H_{27}N_3O_2$ 0.25H$_2$O requires C, 72.47; H, 7.14; N, 10.77%.

EXAMPLE 16

1-(3-Chloro-benzylpiperidin-4-yl)-5-methyl-4-phenyl-1,3-dihydro-imidazol-2-one a) 4-Amino-1-(3-chlorobenzyl)-piperidine

This compound was prepared using the procedure described in Example 8, Step C, using 3-chlorobenzylbromide in place of bromoethylbenzene.

b) 1-(3-Chloro-benzylpiperidine-4-yl)-5-methyl-4-phenyl-1,3-dihydro-imidazol-2-one This compound was prepared using the procedure outlined in Example 1, Method B using 4-amino-1-(3-chlorobenzyl)piperidine instead of 4-amino-1-benzylpiperidine), m.p. 248°–249° C. $^1$H NMR (DMSO) δ 1.61 (2H, d, J=11 Hz), 2.04 (2H, m), 2.19 (3H, s), 2.44 (2H, m), 2.88 (2H, d, J=11 Hz), 3.51 (2H, s), 3.74 (1H, m), 7.23–7.40 (9H, m), 10.26 (1H, s). MS (CI) m/e 382 [MH]$^+$. Anal. found C, 68.86; H, 6.36; N, 10.95. $C_{23}H_{24}N_3OCl.0.1H_2O$ requires C, 69.19; H, 6.33; N, 11.00%.

EXAMPLE 17

1-(3-Bromobenzylpiperidin-4-yl)-5-methyl-4-phenyl-1,3-dihydro-imidazol-2-one This compound was prepared using the procedure described in Example 14, Part c, using 3-bromobenzylbromide instead of α-bromo-m-tolunitrile. m.p. 263–265° C. $^1$H NMR (DMSO) δ 1.61 (2H, d, J=12 Hz), 2.04 (2H, m), 2.19 (3H, s), 2.45 (2H, m), 2.87 (2H, d, J=11 Hz), 3.49 (2H, s), 3.74 (1H, m), 7.21–7.52 (9H, m), 10.25 (1H, s). MS (CI) m/e 427 [MH]$^+$. Anal found C, 61.86; H, 5.61; N, 9.74. $C_{22}H_{24}N_3OBr$ requires C, 61.98; H, 5.67; N, 9.86%.

EXAMPLE 18

1-(3-Iodo-benzylpiperidin-4-yl)-5-methyl-4-phenyl-1,3-dihydro-imidazol-2-one This compound was prepared using the procedure described in Example 14, Part C, using 3-iodobenzylbromide instead of α-bromo-m-tolunitrile. M.p. 269°–271° C. $^1$H NMR (DMSO) δ 1.61 (2H, d, J=10 Hz), 2.03 (2H, m), 2.19 (3H, s), 2.4 (2H, m), 2.87 (2H, d, J=11 Hz), 3.46 (2H, s), 3.74 (1H, m), 7.13–7.4 (7H, m), 7.62 (1H, d, J=8 Hz), 7.69 (1H, s), 10.26 (1H, s). MS (CI) m/e 474 [MH]$^+$. Anal. found C, 55.51; H, 5.14; N, 8.83. $C_{22}H_{24}IN_3O.0.15H_2O$ requires C, 55.82; H, 5.11; N, 8.88%.

EXAMPLE 19

5-Methyl-4-phenyl-1-(1-(3-trifluoromethylbenzyl)-piperidin-4-yl)-1,3-dihydro-imidazol-2-one This compound was prepared in the same way as described for Example 14 c using meta trifluoromethylbenzyl bromide. Mp 243° C. $^1$H NMR (DMSO) δ 1.61 (2H, m), 2.06 (2H, m), 2.20 (3H, s), 2.45 (2H, m), 2.89 (2H, m), 3.60 (2H, s), 3.75 (1H, m), 7.24 (1H, m), 7.33–7.65 (8H, m), 10.26 (1H, br s). MS (CI) m/e 416 [MH]$^+$. Anal. found C, 66.30; H, 5.73; N, 9.97. $C_{23}H_{24}F_3N_3O$ requires C, 75.66; H, 7.27; N, 12.03%.

EXAMPLE 20

1-(1-(2,3-Methylenedioxybenzyl)-piperidin-4-yl)-5-methyl-4-phenyl-1,3-dihydro-imidazol-2-one The product from 14a) (0.6 g, 0.0034 mol) and 2,3-methylenedioxybenzaldehyde (0.51 g, 0.0034 mol) were dissolved in methanol (30 ml) and activated 3 Å sieves (2.5 g) were added. After 30 minutes stirring at room temperature, sodium cyanoborohydride (0.28 g, 0.044 mol) was added and stirring was continued for 14 h. Methanol saturated with dry hydrogen chloride (10 ml) was added and after 1 h the reaction mixture was filtered and concentrated under vacuum. The residue was partitioned between 1N sodium hydroxide solution (20 ml) and brine (20 ml) then dried (MgSO$_4$), filtered and evaporated under vacuum. The residue was purified by elution through a silica column using 0 to 5% methanol in dichloromethane as eluent then recrystallised from methanol/ethyl acetate to give the required product as a white solid(24 mg, 2%), mp 244°–245° C. $^1$H NMR (DMSO$_3$) δ 1.60 (2H, m), 2.05 (2H, m), 2.19 (3H, s), 2.43 (2H, m), 2.92 (2H, m), 3.47 (2H, s), 3.72 (1H, m), 6.00 (2H, s), 6.83 (3H, m), 7.20–7.40 (5H, m), 10.25 (1H, br s). MS (CI) m/e 392 [MH]$^+$. Anal. Found C, 70.13; H, 6.39; N, 10.72. $C_{23}H_{25}N_3O_3.0.1H_2O$ requires C, 70.24; H, 6.46; N, 10.69%.

We claim:

1. A compound of formula I, or a salt thereof or a prodrug thereof:

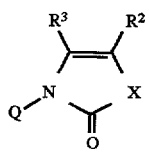

(I)

wherein

X represents oxygen or N—R$^1$;

Q represents a substituted five-, six- or seven-membered monocyclic heteroaliphatic ring which contains one nitrogen atom as the sole heteroatom and is linked to the imidazolone or oxazolone ring via a carbon atom;

R$^1$ represents hydrogen or C$_{1-6}$ alkyl; and one of R$^2$ and R$^3$ represents hydrogen or C$_{1-6}$ alkyl and the other of R$^2$ and R$^3$ represents cycloalkyl or a group of formula (i), (ii) or (iii):

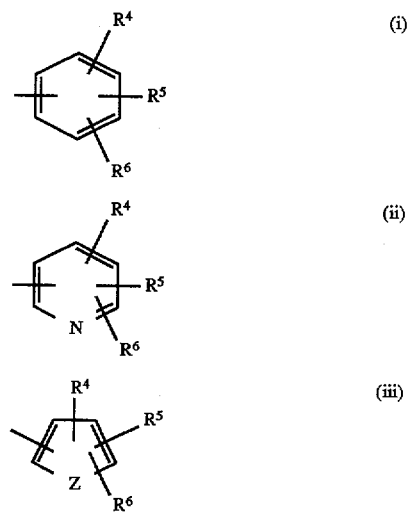

in which Z represents oxygen, sulphur or NH;

R$^4$, R$^5$ and R$^6$ independently represent hydrogen, hydrocarbon, wherein said hydrocarbon is selected from the group consisting of: C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$) alkyl, aryl and aryl(C$_{1-6}$)alkyl, a heterocyclic group, wherein said heterocyclic group is selected from the group consisting of: C$_{3-7}$ heterocycloalkyl, C$_{3-7}$ heterocycloalkyl(C$_{1-6}$)alkyl, heteroaryl and heteroaryl (C$_{1-6}$)alkyl, in which said heteroaryl is selected from the group consisting of: pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl; halogen, cyano, trifluoromethyl, nitro, —OR$^a$, —SR$^a$, —SOR$^a$, SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; and R$^a$ and R$^b$ independently represent hydrogen, hydrocarbon or a heterocyclic group, as defined above.

2. A compound as claimed in claim 1 represented by formula IIA, and pharmaceutically acceptable salts and prodrugs thereof:

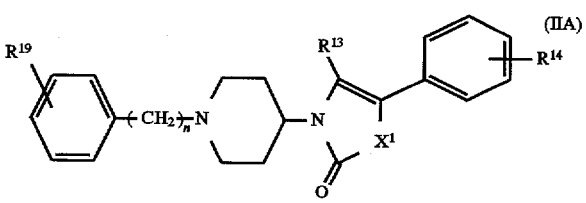

(IIA)

wherein n is zero, 1, 2 or 3;

X$^1$ represents oxygen or N—R$^{11}$;

R$^{11}$ and R$^{13}$ independently represent hydrogen or C$_{1-6}$ alkyl; and

R$^{14}$ and R$^{19}$ independently represent hydrogen, halogen, trifluoromethyl, cyano, nitro, amino, C$_{1-6}$ alkylamino, di(C$_{1-6}$)alkylamino, C$_{1-6}$ alkyl, C$_{1-6}$ alkoxy, aryl (C$_{1-6}$)alkoxy or C$_{2-6}$ alkylcarbonyl.

3. A compound as claimed in claim 1 represented by formula IIB, and pharmaceutically acceptable salts and prodrugs thereof:

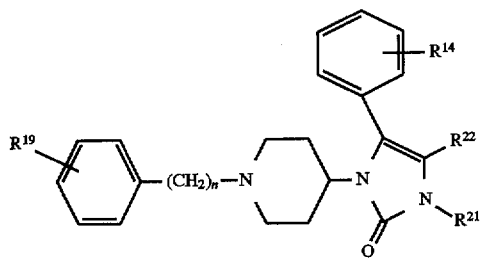
(IIB)

wherein n, $R^{14}$ and $R^{19}$ are as defined in claim 2; and $R^{21}$ and $R^{22}$ independently represent hydrogen or $C_{1-6}$ alkyl.

4. A compound selected from:

1-(1-benzylpiperidin-4-yl)-5-methyl-4-phenyl-1,3-dihydroimidazol-2-one;

1-(1-benzylpiperidin-4-yl)-4-methyl-5-phenyl-1,3-dihydroimidazol-2-one;

1-(1-benzylpiperidin-4-yl)-4-(4-chlorophenyl)-5-methyl-1,3-dihydroimidazol-2-one;

1-(1-benzylpiperidin-4-yl)-5-(4-chlorophenyl)-4-methyl-1,3-dihydroimidazol-2-one;

1-(1-benzylpiperidin-4-yl)-4-phenyl-1,3-dihydroimidazol-2-one;

1-(1-benzylpiperidin-4-yl)-3-methyl-4-phenyl-1,3-dihydroimidazol-2-one;

1-(1-benzylpiperidin-4-yl)-3,5-dimethyl-4-phenyl-1,3-dihydroimidazol-2-one;

5-methyl-4-phenyl-1-[1-(2-phenylethyl)piperidin-4-yl]-1,3-dihydroimidazol-2-one;

5-methyl-1-[1-(2-methylbenzyl)piperidin-4-yl]-4-phenyl-1,3-dihydroimidazol-2-one;

4-(4-chlorophenyl)-5-methyl-1-[1-(2-phenylethyl)-piperidin-4-yl]-1,3-dihydroimidazol-2-one;

4-methyl-5-phenyl-3-[1-(2-phenylethyl)piperidin-4-yl]-3H-oxazol-2-one;

4-(4-chlorophenyl)-5-methyl-1-[1-(2-methylbenzyl)piperidin-4-yl]-1,3-dihydroimidazol-2-one;

5-methyl-1-[1-(2-methylbenzyl)piperidin-4-yl]-4-(4-methylphenyl)-1,3-dihydroimidazol-2-one;

1-[1-(3-cyanobenzyl)piperidin-4-yl]-5-methyl-4-phenyl-1,3-dihydroimidazol-2-one;

1-[1-(3-methoxybenzyl)piperidin-4-yl]-5-methyl-4-phenyl-1,3-dihydroimidazol-2-one;

1-[1-(3-chlorobenzyl)piperidin-4-yl]-5-methyl-4-phenyl-1,3-dihydroimidazol-2-one;

1-[1-(3-bromobenzyl)piperidin-4-yl]-5-methyl-4-phenyl-1,3-dihydroimidazol-2-one;

1-[1-(3-iodobenzyl)piperidin-4-yl]-5-methyl-4-phenyl-1,3-dihydroimidazol-2-one;

5-methyl-4-phenyl-1-[1-(3-trifluoromethylbenzyl)piperidin-4-yl]-1,3-dihydroimidazol-2-one;

5-methyl-1-[1-(2,3-methylenedioxybenzyl)piperidin-4-yl]-4-phenyl-1,3-dihydroimidazol-2-one;

and pharmaceutically acceptable salts and prodrugs thereof.

5. A pharmaceutical composition comprising a compound as claimed in claim 1 in association with a pharmaceutically acceptable carrier.

6. A method for the treatment and/or prevention of schizophrenia which method comprises administering to a patient in need of such treatment an effective amount of a compound as claimed in claim 1.

7. A process for the preparation of a compound as claimed in claim 1, wherein X is NH, which comprises reacting a compound of formula III with a compound of formula IV:

(III)

(IV)

wherein Q, $R^2$ and $R^3$ are as defined in claim 1; followed, if necessary, by separation of the resulting mixture of isomers; and subsequently, if desired, converting a compound of formula I initially obtained into a further compound of formula I by conventional methods.

8. A process for the preparation of a compound as claimed in claim 1, wherein X represents N—$R^1$, which comprises reacting a compound of formula $R^{10}$—N=C=O with a compound of formula V:

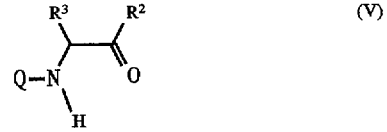
(V)

wherein Q, $R^2$ and $R^3$ are as defined in claim 1, and $R^{10}$ corresponds to the group $R^1$ or represents an amino-protecting group; followed, where necessary, by removal of the amino-protecting group $R^{10}$; and subsequently, if desired, N-alkylation by standard methods to introduce the moiety $R^1$; and also, where required, converting a compound of formula I initially obtained into a further compound of formula I by conventional methods.

9. A process for the preparation of a compound as claimed in claim 1, wherein X is oxygen, which comprises reacting a compound of formula V with a compound of formula $L^2$—CO—$L^3$:

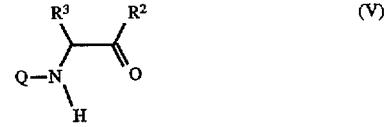
(V)

wherein Q, $R^2$ and $R^3$ are as defined in claim 1 and $L^2$ and $L^3$ independently represent suitable leaving groups; and subsequently, if desired, converting a compound of formula I initially obtained into a further compound of formula I by conventional methods.

* * * * *